United States Patent [19]

Naganuma

[11] Patent Number: 5,688,250
[45] Date of Patent: *Nov. 18, 1997

[54] SYRINGE

[75] Inventor: Masateru Naganuma, Kanagawa, Japan

[73] Assignee: Seikagaku Kogyo Kabushiki Kaisha (Seikagaku Corporation), Tokyo, Japan

[*] Notice: The term of this patent shall not extend beyond the expiration date of Pat. No. 5,468,232.

[21] Appl. No.: 482,856

[22] Filed: Jun. 7, 1995

Related U.S. Application Data

[63] Continuation of Ser. No. 966,199, filed as PCT/JP92/00951, Jul. 24, 1992, Pat. No. 5,468,232.

[30] Foreign Application Priority Data

Jul. 26, 1991 [JP] Japan ........................... 3-209862

[51] Int. Cl.$^6$ .......................... A61M 5/24; A61M 5/28
[52] U.S. Cl. .......................... 604/200; 604/201; 604/210
[58] Field of Search .......................... 604/218, 187, 604/220, 224, 197, 200, 201, 221, 227, 198, 232, 213, 165, 110, 164, 263, 228, 229, 241, 242, 209–211, 82–94, 905; 128/763, 919

[56] References Cited

U.S. PATENT DOCUMENTS

| 1,852,658 | 4/1932 | Kile | 604/209 |
|---|---|---|---|
| 2,375,711 | 5/1945 | Vondrak | 604/210 |
| 2,453,590 | 11/1948 | Poux | 604/201 |
| 2,752,920 | 7/1956 | Kurkjian | 604/218 |
| 2,875,761 | 3/1959 | Helmer et al. | 604/210 |
| 3,604,267 | 9/1971 | Johns . | |
| 3,678,931 | 7/1972 | Cohen | 604/201 X |
| 4,314,556 | 2/1982 | Ma . | |
| 4,364,388 | 12/1982 | Cech | 604/209 |
| 4,932,947 | 6/1990 | Cardwell | 604/198 |
| 5,004,124 | 4/1991 | Stefaniak et al. | 222/136 |
| 5,024,616 | 6/1991 | Ogle, II | 604/192 |
| 5,080,649 | 1/1992 | Vetter | 604/91 |
| 5,344,409 | 9/1994 | Ennis, III et al. | 604/210 |
| 5,531,708 | 7/1996 | Woodruff | 604/208 |

FOREIGN PATENT DOCUMENTS

| 2627087 | 8/1989 | France . |
| 1954509 | 5/1971 | Germany . |
| 63-92600 | 6/1988 | Japan . |
| 255958 | 4/1990 | Japan . |
| 286556 | 7/1990 | Japan . |

OTHER PUBLICATIONS

Page from Catalogue of Senju Pharmaceutical Co., Ltd., of Japan, dated May, 1995.

*Primary Examiner*—Michael Powell Buiz
*Assistant Examiner*—A. T. Nguyen
*Attorney, Agent, or Firm*—Sughrue,Mion,Zinn,Macpeak & Seas, PLLC

[57] ABSTRACT

A cartridge-type syringe in which a cartridge, having liquid medicine or the like sealed therein, is inserted in a holder having a discharge needle at its distal end, and the cartridge is advanced to cause the discharge needle to pierce it, thereby injecting the liquid medicine or the like into an object, and when a piston rod of the cartridge is pushed to cause the discharge needle to pierce, the liquid medicine or the like will not be discharged in error in a large amount. In particular, there is provided a releaseable lock mechanism by which when a piston rod 15 is pushed, the piston rod 15 advances together with a tubular body 11 of a cartridge 10 without moving a piston 14 within the tubular body 11. For example, in a first embodiment, when a discharge needle 5 pierces the distal end of the tubular body 11, an engagement member 24 is pressed to be brought into intimate contact with the piston rod 15, thereby releasing the lock mechanism 21, and by pushing the piston rod 15, the piston 14 is driven to advance within the tubular body 11, thereby discharging liquid medicine or the like via the discharge needle 5.

5 Claims, 3 Drawing Sheets

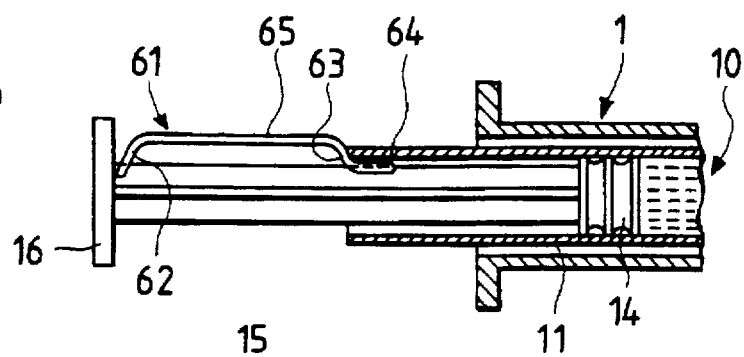
FIG. 9
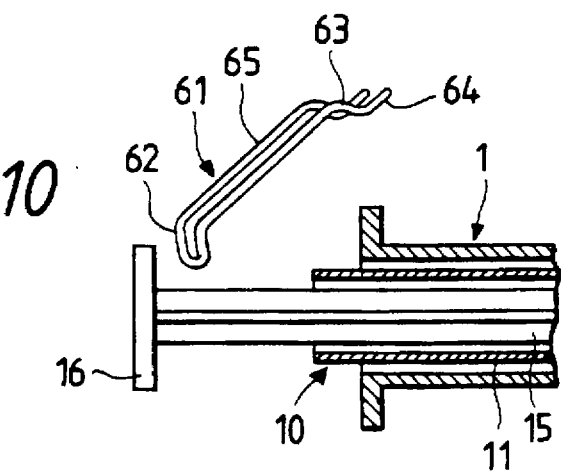
FIG. 10
FIG. 11 PRIOR ART
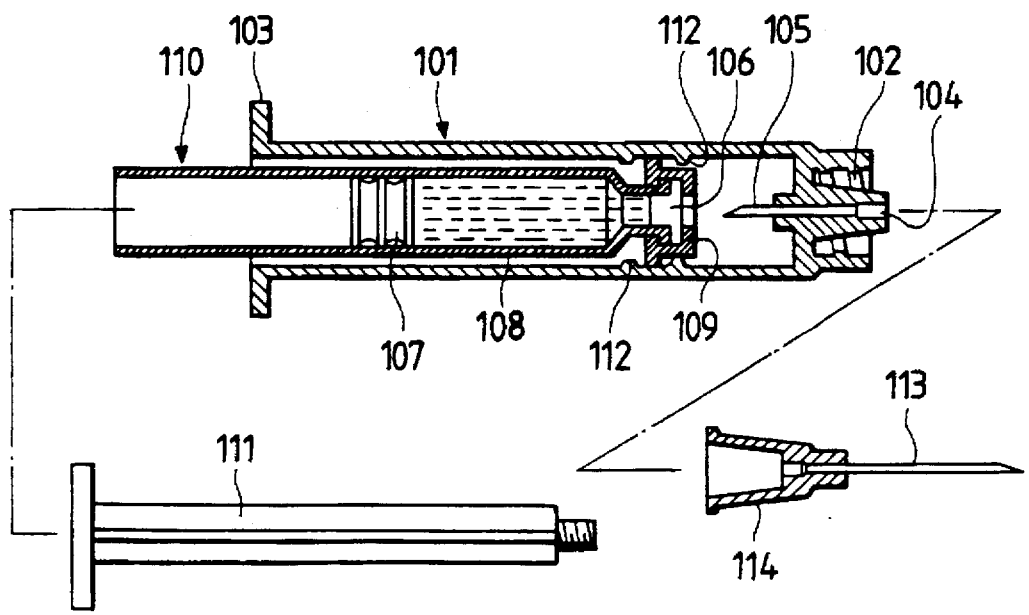

SYRINGE

This is a continuation of application Ser. No. 07/966,199 filed Jan. 27, 1993 now U.S. Pat. No. 5,468,232 which is a 371 of PCT/JP92/00951 filed Jul. 24, 1992.

TECHNICAL FIELD

This invention relates to a syringe of the type in which a cartridge, having a liquid medicine, an adhesive or the like sealed therein, is fitted in a holder, and in use, the cartridge is advanced to cause a discharge needle to pierce a distal end thereof, and subsequently a piston is advanced to inject the liquid medicine or the like into a human body or other object via the discharge needle and an injection needle.

BACKGROUND ART

As shown in FIG. 11, generally, a cartridge-type syringe suited for disposable purposes comprises a cylindrical holder 101 which has at its distal end a mounting portion 102, constituted by a lock adapter to which a needle proximal portion 114 of an injection needle 113 is adapted to be connected, and a flange 103 at its proximal end, a discharge needle 105 fixedly fitted liquid-tight in a through hole 104, formed through a central portion of the mounting portion 102, with a pointed end thereof extended into the interior of the holder 101, a cartridge 110 which comprises a cylindrical tubular body 108 closed at its open distal end by a closure member 106 of rubber, and a piston 107 fitted liquid-tight into this tubular body to a predetermined position from an open proximal end thereof, and a predetermined amount of liquid medicine or the like sealed in the tubular body, and a piston rod 111 to be connected to the piston 107. A flange of a cap 109 fixedly holding the closure member 106 is disposed between front and rear projections 112 formed on the inner peripheral surface of the holder 101, so that the cartridge 110 fitted in the holder 101 is provisionally held in a position where the closure member 106 is spaced apart from the discharge needle 105 (Japanese Laid-Open Utility Model Application No. 2-55958).

In order to avoid a disadvantage that the piston rod 111 is inadvertently pushed to inject the liquid medicine or the like, for example, during transport, the piston rod 111 is separate, and after the tubular body 108 is pushed to cause the discharge needle 105 to pierce it, the piston rod 111 is intended to be connected to the piston 107 so as to effect the injection to the object. However, there is a fixed conception that the piston rod in the syringe is to be pushed, and therefore in most cases, the piston rod 111 is first connected to the piston 107, and the needle proximal portion 114 is connected to the mounting portion 102 to attach the injection needle 113 to the holder 101, and then the piston rod 111 is pushed to advance the tubular body 108 together with it to release the provisional holding condition achieved by the projections 112, to cause the discharge needle 105 to pierce the closure member 106, and the piston rod 111 is further pushed to advance the piston 107 within the tubular body 108, thereby injecting the medicine or the like into the object via the discharge needle 105 and the injection needle 113.

Namely, in this conventional syringe, when the piston rod 111 is pushed, the tubular body 108 is advanced together with it since the liquid medicine or the like is sealed in a liquid tight manner, and it is necessary to apply a considerable force to the piston rod 111 in order to cope with a resistance offered when the discharge needle 105 pierces the closure member 106, and therefore the liquid medicine or the like is in a pressurized condition. Therefore, when the discharge needle 105 completely pierces the closure member 106, the liquid medicine or the like is discharged through the discharge needle 105, and in addition the liquid may leak from a gap between the closure member 106 and the discharge needle 105. And besides, when the complete piercing is achieved, the resistance is abruptly reduced, and the tubular body 108 is abutted against the distal end of the holder 101, and is stopped, and therefore the piston rod 111 may be pushed greatly, so that the liquid medicine is discharged in error in a large amount, which invites a disadvantage that the amount of injection into the object is greatly reduced.

Moreover, it is inconvenient to connect the piston rod 111 to the piston each time it is used.

Further, the reduced amount of injection into the object, which is caused by the wasteful discharge of the liquid medicine or the like, lowers the effect accordingly.

In the conventional cartridge-type syringe comprising the tubular holder having the injection needle-mounting portion at its distal end, the discharge needle fixedly mounted on the mounting portion with its pointed end extended into the holder, and the cartridge which comprises the tubular body of a predetermined length, the closure member mounted on the open distal end and pierceable by the discharge needle, the piston inserted to the predetermined position from the open proximal end, and the liquid medicine or the like sealed by these parts, wherein the cartridge is fitted in the holder so as to move back and forth, and is held in the position where the closure member is spaced apart from the discharge needle, the piercing of the discharge needle through the closure member by the pushing of the piston rod and the discharge of the liquid medicine or the like are effected in a continuous single operation, and therefore the liquid medicine or the like is liable to be discharged in error in a large amount, so that the amount of injection into the object is reduced, and besides since the piston rod is separate from the piston, they must be connected together each time they are used, and this is inconvenient. The problems to be solved by the present invention are these points.

DISCLOSURE OF THE INVENTION

In order to solve the above problems, the present invention is characterized in that a piston of a cartridge is beforehand provided with a piston rod projected from a proximal end of a tubular body, that the tubular body is of such a length that when the tubular body is inserted a maximum depth into the holder, the proximal end will not be received in the holder, and that utilizing this construction, a releaseable lock mechanism for preventing the piston from advancing within the tubular body is provided on the piston rod, and this means achieves an object which is to provide a syringe which overcomes the disadvantage that the liquid medicine or the like is discharged in error, and overcomes the inconvenience in use.

More specifically, the present invention provides a syringe comprising a tubular holder having an injection needle-mounting portion provided at a distal end thereof; a discharge needle fixedly mounted on the mounting portion with its pointed end extended into the holder; and a cartridge including a tubular body of a predetermined length, a closure member which is mounted on an open distal end of the tubular body, and is pierceable by the discharge needle, a piston inserted to a predetermined position from an open proximal end, and a liquid medicine or the like sealed by these parts, the cartridge being fitted in the holder so as to move back and forth, and being disposed at a position where the closure member is spaced apart from the discharge needle;

characterized in that the piston has a piston rod; the tubular body is of such a length that when the tubular body is inserted a maximum depth into the holder, the proximal end thereof is not completely received in the holder; and a releaseable lock mechanism for preventing the piston from advancing within the tubular body is provided on the piston rod or the tubular body.

Preferred embodiments of the present invention are as follows:

In a first embodiment of the syringe, the lock mechanism comprises an axially-extending notch formed in that portion of the piston rod projected from the tubular body, an engagement member fitted in the notch in such a manner that the engagement member is not projected from the surface of the piston rod, and a plurality of sets of connection portions arranged in the axial direction to connect the engagement member to the piston rod, wherein when those of the connection portions which are closest to the tubular body are incompletely connected, a distal end face of the engagement member is engaged with a proximal end face of the tubular body.

In a second embodiment of the syringe, the lock mechanism comprises an engagement member axially-movably fitted on that portion of the piston rod projected from the tubular body, and a releaseable connection portion for fixing the engagement member to the piston rod at a position where the engagement member is held against a proximal end face of the tubular body.

In a third embodiment of the syringe, the lock mechanism comprises an arm member which is hingedly connected to the proximal end of the tubular body, and extends axially along that portion of the piston rod projected from the tubular body, and an engagement piece which is formed on the engagement arm, and is releaseably engaged with a proximal end head of the piston rod.

In a fourth embodiment of the syringe, the lock mechanism comprises a spacing holder member which is removably mounted on that portion of the piston rod projected from the tubular body in such a manner that the opposite ends of the spacing holder member are engaged with a proximal end head of the piston rod and a distal end face of the tubular body, respectively.

The piston rod is projected a predetermined distance from the tubular body, and is fixed in this position by the lock mechanism, and in this condition the shipment, the transport and the storage are done. In use, when the piston rod is pushed, the tubular body is driven to advance together with it to cause the discharge needle to pierce it, and when the tubular body is inserted a maximum depth into the holder, it is stopped, and the piston rod is also stopped. At this time, the piston does not pressurize the liquid medicine or the like, and it is stopped simultaneously when the tubular body is stopped, and therefore the liquid medicine or the like is not discharged. Then, the lock mechanism is released, and by pushing the piston rod, the liquid medicine in the cartridge is injected into an object.

BRIEF DESCRIPTION OF THE DRAWINGS

FIG. 9 is a longitudinal cross-sectional view of a portion of an example of a fourth invention. FIG. 10 is a longitudinal cross-sectional view of a portion of the fourth invention in a liquid medicine discharge condition. FIG. 11 is a longitudinal cross-sectional view of the conventional example.

DETAILED DESCRIPTION OF THE INVENTION

EXAMPLE 1

Figure 1:
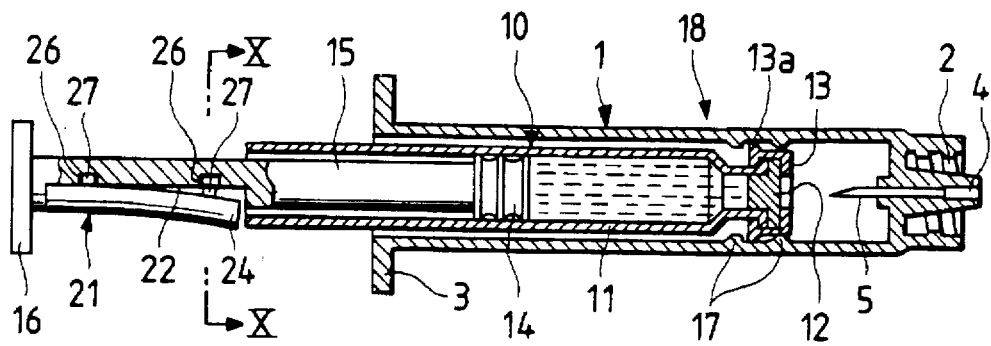
FIG. 1 a longitudinal cross-sectional view of an example of a first invention.

A first embodiment of the present invention will now be described with reference to FIGS. 1, 2 and 3. A cylindrical holder 1 includes a mounting portion 2 at its distal end which is constituted by a lock adapter, and a flange 3 at its proximal end. A through hole 4 is formed through a central portion of the mounting portion 2, and a discharge needle 5 is fixedly fitted liquid-tight in the through hole 4 with its pointed end extended into the interior of the holder 1.

A cartridge 10 comprises a cylindrical tubular body 11 having a closure member 12 of rubber sealingly fitted on an open distal end thereof, a ring-shape cap 13 fixedly holding the closure member 12, and a piston 14 inserted to a predetermined position from an open proximal end, and a predetermined amount of liquid medicine sealed in a space formed by these parts. The cartridge is loosed inserted into the holder 1 from the proximal end. The tubular body 11 of the cartridge 10 is of such a length that when this tubular body is inserted a maximum depth into the holder 1, the proximal end face thereof is disposed flush with or slightly projected from the proximal end face of the holder 1. The piston 14 has an integral piston rod 15 in the form of a rounded rod which is projected from the proximal end of the tubular body 11.

Front and rear projections 17, 17 between which a small gap is provided are formed on the inner peripheral surface of the holder 1, and a flange 13a of the cap 13 is disposed between the projections 17, 17, so that the cartridge 10 is held in such a position that the closure member 12 is spaced apart from the point end of the discharge needle 5. The projections 17, 17 and the flange 13a constitute a provisional holder means 18 for the cartridge 10.

A lock mechanism 21 is constituted by an axially-extending notch 22 which has a crescent shape as viewed from its end face, and is formed by cutting part of that portion of the piston rod 15 projected from the tubular body 11, an engagement member 24 which is fitted in the notch 22 without being projected from the piston rod 15 to form a common surface together with it, and has a crescent shape as viewed from its end face, and has the same length as that of the notch 22, a plurality of (for example, two) holes 26 which are formed in a flat surface 23 of the notch 22, and are spaced axially at a suitable interval, and a plurality of (for example, two) projections 27 which are formed on a flat surface 25 of the engagement member 24, and are opposed to the holes 26, respectively. Both of the piston rod 15 and the engagement member 24 are made of a rigid synthetic resin.

The projection 27 opposed to the hole 26 closer to a proximal end head 16 of the piston rod 15 is completely pressed and fitted into this hole, and the projection 27 opposed to the hole 26 closer to the tubular body 11 is partially fitted in this hole. With this arrangement, the distal end face of the engagement member 24 is held in contact with the proximal end face of the tubular body 11.

Figure 2:
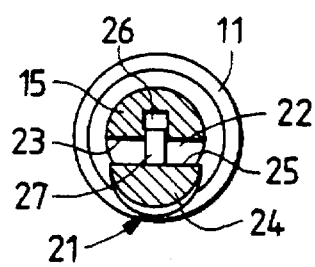
FIG. 2 is an enlarged cross-sectional view taken along the line X—X of FIG. 1.

In use, when the proximal end head 16 of the piston rod 15 is pushed in the condition in which the engagement member 24 is held in engagement with the tubular body 11 as shown in FIGS. 1 and 2, the flange 13a slides over the front projection 17 to pass past it, and then the discharge needle 5 pierces the closure member 12, and the tubular body 11 is abutted at its distal end against the distal end of the holder 1, and is stopped. The piston rod 15 advances together with the tubular body 11, and when the tubular body 11 is stopped, the piston rod 15 can not be pushed. Therefore, the piston 14 will not pressurize the liquid medicine, so that it will not be discharged or leak.

Figure 3:
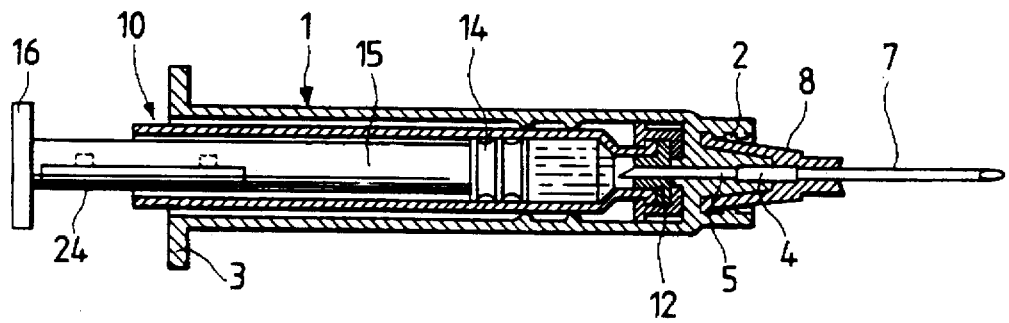
FIG. 3 is a longitudinal cross-sectional view of the first invention in a liquid medicine discharge condition.

Then, a needle proximal portion 8 of the injection needle 7 is connected to the mounting portion 2, the distal end portion of the engagement member 24 is strongly pressed to bring the partially-fitted projection 27 into complete fitting engagement with the hole 26, thereby releasing the lock mechanism 21, and the injection needle 7 is pierced into an object such as a human body, and the piston rod 15 is pushed to advance the piston 14 within the tubular body 11, thereby injecting the liquid medicine into the object (the body or the like) via the discharge needle 5 and the injection needle 7 (FIG. 3). At this time, the engagement member 24 constitutes part of the piston rod 15, and enters the tubular body 11.

EXAMPLE 2

Figure 4:
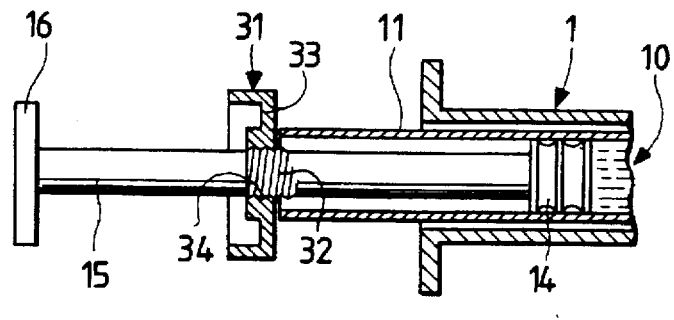
FIG. 4 is a longitudinal cross-sectional view of a portion of an example of a second invention.
Figure 5:
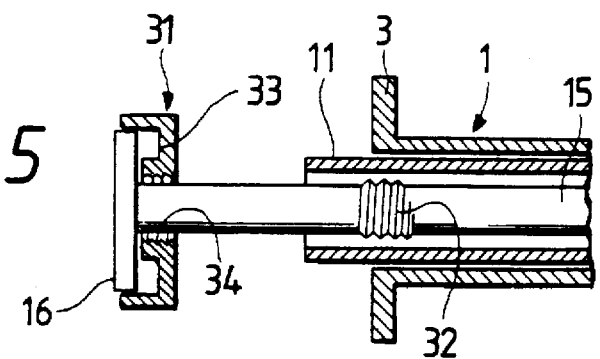
FIG. 5 is a longitudinal cross-sectional view of a portion of the second invention in a liquid medicine discharge condition.

FIGS. 4 and 5 show an example of a second embodiment of the present invention. Since a holder 1 and a cartridge 10 are the same as those in Example 1, they are omitted, and a lock mechanism 31 is mainly shown.

The lock mechanism 31 comprises a threaded portion 32 formed on that portion of a piston rod 15 (which is in the form of a rounded rod) which extends from the vicinity of a proximal end face of a tubular body 11 to a position slightly projected from this proximal end face, and a disk-shaped engagement member 33 having a central threaded hole 34. The engagement member 33 is held against the proximal end face of the tubular body 11, with the threaded hole 34 threadedly engaged with the threaded portion 32. In this Example, both of the piston rod 15 and the engagement member 33 are made of a rigid synthetic resin.

The threaded portion 32 and the threaded hole 34 constitute the releaseable connection portion, and the diameter of the groove portion in the threaded portion 32 is equal to or larger than the diameter of the piston rod 15, and the engagement member 33 is movable on the piston rod 15. These threads are left threads, and when the engagement member 33 is habitually rotated right, it is moved toward the proximal end of the piston rod 15, and is released.

In this Example, the piston rod 15 is pushed to advance the tubular body together with this piston rod to cause a discharge needle to pierce it, and then the engagement member 33 is disengaged from the threaded portion 32 to release the lock mechanism 31, and the piston rod 15 is pushed to inject liquid medicine into an object (such as a body). At this time, the engagement member 33 has been moved into contact with the proximal end head 16 as shown in FIG. 5, or it is free on the piston rod 15.

EXAMPLE 3

Figure 6:
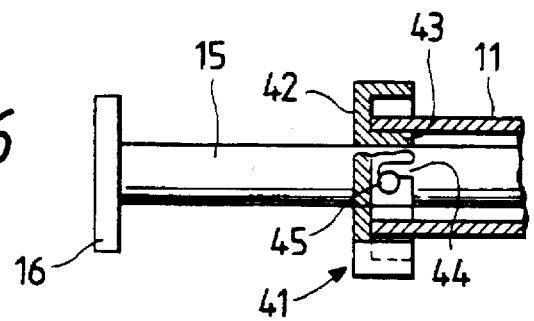
FIG. 6 is a longitudinal cross-sectional view of a portion of another example of the second invention.

FIG. 6 shows another example of the second embodiment of the present invention. In this Example, a lock mechanism 41 comprises a pin 45 formed on and projected from a piston rod 15, and an engagement member 42 having a boss 43 having an L-shaped groove 44 relative to which the pin is engaged or connected. The boss 43 is fitted on the piston rod 15 for axial movement, and is received in a gap between a tubular body 11 and the piston rod. The engagement member 42 is held against the proximal end face of the tubular body 11 with the pin 45 engaged in the engagement groove 44, and in this condition the engagement member 42 is releaseably fixed to the piston rod 15. The pin 45 and the engagement groove 44 in the engagement member 42 constitute a releaseable connection portion, and by slightly rotating the engagement member 42 to move the same toward the proximal end, the engagement groove 44 is disengaged from the pin 45, so that the engagement member is freely movable on the piston rod 15. In this Example, both of the piston rod 15 and the engagement member 42 are made of a rigid synthetic resin.

EXAMPLE 4

Figure 7:
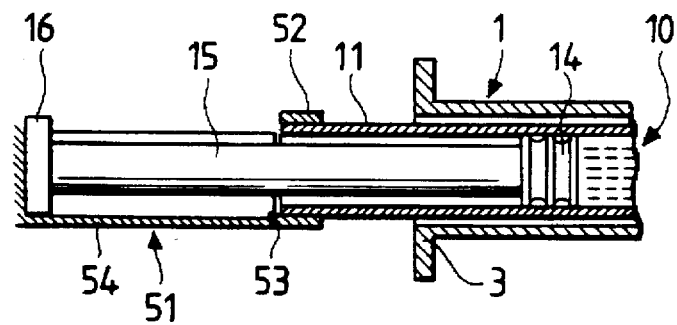
FIG. 7 is a longitudinal cross-sectional view of a portion of an example of a third invention.
Figure 8:
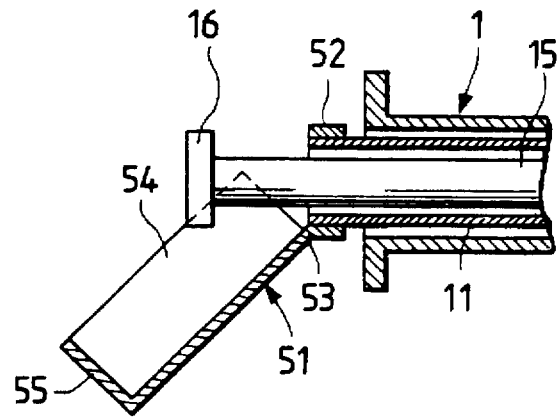
FIG. 8 is a longitudinal cross-sectional view of a portion of the third invention in a liquid medicine discharge condition.

FIGS. 7 and 8 show an example of a third embodiment of the present invention. In this Example, a lock mechanism 51 comprises an annular base piece 52 fixedly fitted on an outer peripheral surface of a proximal end of a tubular body 11, an arm member 54 which has a U-shape as viewed from its end face, and is pivotally connected at one end to the base piece 52 by a hinge 53, and an engagement piece 55 integrally formed at the other end to cover the U-shaped end face. The arm member 54 extends axially, and half surrounds that portion of a piston rod 15 projected from the tubular body 11, and the engagement piece 55 is engaged with a proximal end head 16 in overlapping relation thereto. The base piece 52, the arm member 54 and the engagement piece 55 are made of a rigid synthetic resin.

In the above condition, when the piston rod 15 is pushed, the tubular body 11 advances together with it, and when the arm member 54 is pivotally moved about the hinge 53 to disengage the engagement piece 55 from the proximal end head 16 to release the lock mechanism 51, liquid medicine can be injected into an object (such as a body) by pushing the piston rod 15.

EXAMPLE 5

FIGS. 9 and 10 show an example of a fourth embodiment of the present invention. In this Example, a lock mechanism 61 comprises a spacing holder member 65 which is formed by folding back one metal wire at its central portion to provide parallel sections, and one end thereof is bent as at 62, and a bent portion 63 and an insertion portion 64 extending forwardly of this bent portion 63 are formed at the other end portion. The bent portion 62 is contacted and engaged with a proximal end head 16, and the bent portion 63 is contacted and engaged with a proximal end face of a tubular body 11, and the insertion portion 64 is inserted into the tubular body 11 through a gap between the tubular body and the piston rod 15. Thus, the spacing holder member is mounted on that portion of the piston rod 15 projected from the tubular body 11.

In the above condition, when the piston rod 15 is pushed, the tubular body 11 advances together with it, and when the spacing holder member 65 is removed to release the lock mechanism 61, liquid medicine can be injected into an object (such as a body) by pushing the piston rod 15.

Even after the lock mechanisms 21, 31, 41 and 51 in Examples 1 to 4 are released, they are retained on the piston rod 15 or the tubular body 11, and thus they are not scattered around, and advantageously they can be disposed of together with the syringe. However, depending on the place where the injection is used, such as that other than an operation room, a lock mechanism that can be completely separated, such as the lock mechanism 61 of Example 5, can be used without any problem.

The main object of the present invention is to stop the piston rod 15 when the discharge needle 15 pierces the closure member 12 of the cartridge 10, thereby preventing the liquid medicine from being accidentally discharged, and the construction of the lock mechanism for achieving this object, of course, is not limited to those of the above Examples. Further, in the Examples, although the syringes using the liquid medicine for a human body have been described, they can be similarly applied, for example, to the case where an adhesive is injected into a narrow space.

Capability of Exploitation in Industry

In the present invention, there is provided the releaseable lock mechanism which fixes the piston rod at the position where the piston rod is projected a predetermined distance from the tubular body, thereby preventing the piston from advancing within the tubular body. Therefore, when the piston rod is to be used, no time and labor are needed for connecting the piston rod to the piston, and besides when the piston rod is pushed to cause the discharge needle to pierce the cartridge, and when the cartridge is inserted the maximum depth into the holder, the piston rod is stopped by the lock mechanism, and therefore the piston will not pressurize the liquid medicine or the like, and is stopped together with the tubular body, thereby preventing the discharge of the liquid medicine.

Namely, the disadvantage that the operation for causing the discharge needle to pierce the cartridge by the lock mechanism and the operation for releasing the lock mechanism to drive the piston to discharge the liquid medicine or the like are carried out as two separate, discontinuous operations, respectively, as well as the disadvantage that when the discharge needle is caused to pierce, the liquid medicine or the like is discharged in error in a large amount, so that the amount of injection into the object is reduced to lower the effect, is eliminated, and the predetermined amount of the liquid medicine or the like can be properly administered or injected.

I claim:

1. A syringe comprising a tubular holder defining an interior and having an injection needle-mounting portion provided at a distal end thereof; a discharge needle fixedly mounted on said mounting portion with its pointed end extended into the interior of said holder; and a cartridge including a tubular body of a predetermined length, a closure member which is mounted on an open distal end of said tubular body, and is pierceable by said discharge needle, a piston inserted to a predetermined position from an open proximal end, and a liquid sealed by said tubular body, said closure member and said piston, said cartridge being fitted in said holder so as to move back and forth within the interior of said holder, and being disposed at a position where said closure member is spaced apart from said discharge needle;

wherein said piston includes a piston rod; and said tubular body is of such a length that when said tubular body is inserted a maximum depth into said holder, the proximal end thereof is not completely received in said holder; and further comprising means for releasably locking said piston rod and in turn said piston with respect to said tubular body of said cartridge such that said piston advances together with said tubular body when said cartridge is advanced so as to pierce said closure member with said discharge needle, said means for releasably locking comprising an engagement member axially-movably fitted on that portion of said piston rod projected from said tubular body, and a releasable connection portion for fixing said engagement member to said piston rod at a position where said engagement member is held against a proximal end face of said tubular body, such that said engagement member is in a locked state during piercing of said closure member with said discharge needle, and is in a released state during injection of the liquid.

2. A syringe comprising a tubular holder defining an interior and having an injection needle-mounting portion provided at a distal end thereof; a discharge needle fixedly mounted on said mounting portion with its pointed end extended into the interior of said holder; and a cartridge including a tubular body of a predetermined length, a closure member which is mounted on an open distal end of said tubular body, and is pierceable by said discharge needle, a piston inserted to a predetermined position from an open proximal end, and a liquid sealed by said tubular body, said closure member and said piston, said cartridge being fitted in said holder so as to move back and forth within the interior of said holder, and being disposed at a position where said closure member is spaced apart from said discharge needle; wherein said piston includes a piston rod; and said tubular body is of such a length that when said tubular body is inserted a maximum depth into said holder, the proximal end thereof is not completely received in said holder; and further comprising means for releasably locking said piston rod and in turn said piston with respect to said tubular body of said cartridge such that said piston advances together with said tubular body when said cartridge is advanced so as to pierce said closure member with said discharge needle, in which said means for releasably locking comprises an axially-extending notch formed in a portion of said piston rod projected from said tubular body, an engagement member fitted in said notch in such a manner that said engagement member is not projected from the surface of said piston rod when said means for releasably locking is in a released state, and a plurality of sets of connection portions arranged in the axial direction to connect said engagement member to said piston rod, wherein when those of said connection portions which are closest to said tubular body are incompletely connected, a distal end face of said engagement member is engaged with a proximal end face of said tubular body.

3. A syringe comprising a tubular holder defining an interior and having an injection needle-mounting portion provided at a distal end thereof; a discharge needle fixedly mounted on said mounting portion with its pointed end extended into the interior of said holder; and a cartridge including a tubular body of a predetermined length, a closure member which is mounted on an open distal end of said tubular body, and is pierceable by said discharge needle, a piston inserted to a predetermined position from an open proximal end, and a liquid sealed by said tubular body, said closure member and said piston, said cartridge being fitted in said holder so as to move back and forth within the interior of said holder, and being disposed at a position where said closure member is spaced apart from said discharge needle; wherein said piston includes a piston rod; and said tubular body is of such a length that when said tubular body is inserted a maximum depth into said holder, the proximal end thereof is not completely received in said holder; and further comprising means for releasably locking said piston rod and in turn said piston with respect to said tubular body of said cartridge such that said piston advances together with said tubular body when said cartridge is advanced so as to pierce said closure member with said discharge needle, in which said means for releasably locking comprises an arm member which is hingedly connected to the proximal end of said tubular body, and extends axially along that portion of said piston rod projected from said tubular body, and an engagement piece which is formed on said engagement arm, and is releasably engaged with a proximal end head of said piston rod.

4. A syringe comprising a tubular holder defining an interior and having an injection needle-mounting portion provided at a distal end thereof; a discharge needle fixedly mounted on said mounting portion with its pointed end extended into the interior of said holder; and a cartridge including a tubular body of a predetermined length, a closure member which is mounted on an open distal end of said tubular body, and is pierceable by said discharge needle, a piston inserted to a predetermined position from an open proximal end, and a liquid sealed by said tubular body, said closure member and said piston, said cartridge being fitted in said holder so as to move back and forth within the interior of said holder, and being disposed at a position where said closure member is spaced apart from said discharge needle;

wherein said piston includes a piston rod; and said tubular body is of such a length that when said tubular body is inserted a maximum depth into said holder, the proximal end thereof is not completely received in said holder; and further comprising an arm member which is hingedly connected to the proximal end of the tubular body and which extends axially along that portion of said piston rod projected from said tubular body, and an engagement piece which is formed on said arm member and is releaseably engaged with a proximal end head of said piston rod, such that when said engagement piece is engaged with said piston rod, said piston advances together with said tubular body as said cartridge is advanced so as to pierce said closure member with said discharge needle.

5. A syringe according to claim 4, wherein said arm member is U-shaped as viewed from an end face thereof.

* * * * *